United States Patent
Wang

(10) Patent No.: US 10,292,855 B2
(45) Date of Patent: May 21, 2019

(54) ORTHOSIS DEVICE AND THREAD-GUIDING STRUCTURE THEREOF

(71) Applicant: Yu-Chien Wang, Taichung (TW)

(72) Inventor: Yu-Chien Wang, Taichung (TW)

( * ) Notice: Subject to any disclaimer, the term of this patent is extended or adjusted under 35 U.S.C. 154(b) by 401 days.

(21) Appl. No.: 15/147,188

(22) Filed: May 5, 2016

(65) Prior Publication Data
US 2017/0319371 A1 Nov. 9, 2017

(51) Int. Cl.
*A61F 5/02* (2006.01)
*F16H 19/00* (2006.01)

(52) U.S. Cl.
CPC ........... *A61F 5/028* (2013.01); *F16H 19/003* (2013.01)

(58) Field of Classification Search
CPC .. A61F 5/028; A61F 5/02; A61F 5/022; A61F 5/024; A61F 5/026; A61F 5/03; F16H 19/003
See application file for complete search history.

(56) References Cited

U.S. PATENT DOCUMENTS

| | | | | |
|---|---|---|---|---|
| 3,834,048 | A * | 9/1974 | Maurer | A43C 11/16 24/575.1 |
| 7,201,727 | B2 | 4/2007 | Schwenn et al. | |
| 7,287,304 | B2 * | 10/2007 | Zebe, Jr. | A43C 7/04 24/134 P |
| 8,516,662 | B2 * | 8/2013 | Goodman | A43C 11/165 24/68 SK |
| 2018/0085243 | A1 * | 3/2018 | Burke | A61F 5/028 |

* cited by examiner

*Primary Examiner* — Kari K Rodriquez
(74) *Attorney, Agent, or Firm* — Muncy, Geissler, Olds & Lowe, P.C.

(57) ABSTRACT

An orthosis device includes thread-guiding structures, two board portions spacingly arranged and at least one rope body. The thread-guiding structure includes: a base having a recess, the inner wall of the recess having a first restriction structure; a guiding member, including a guiding groove arcuately extending and a second restriction structure, received in the recess and positionably restricted with blocking of the first and second restriction structures, the guiding groove and the inner wall defining a thread-penetrating passage therebetween. Each of the two board portions has at least one base. Each of the at least one rope body is disposed through the thread-penetrating passage and arranged in two of the guiding grooves, wherein an axial movement of the at least one rope body operates to drive the two board portions close to or away from each other.

9 Claims, 6 Drawing Sheets

ORTHOSIS DEVICE AND THREAD-GUIDING STRUCTURE THEREOF

BACKGROUND OF THE INVENTION

Field of the Invention

The present invention relates to an orthosis device and a thread-guiding structure thereof.

Description of the Prior Art

Usually, a thread-guiding structure may be seen on a protective apparatus or an orthosis device such as a waist protector, the thread-guiding structure is used to adjust the tightness of the protective apparatus or the orthosis device. This type of waist protector is disclosed in U.S. Pat. No. 7,201,727.

However, in this type of conventional orthosis device and the thread-guiding structure thereof, the thread-guiding structure requires at least one bearing, a spindle and an upper cover and other elements to be operable, and there are many elements in the prior art, and the elements may get lost easily. Therefore, the conventional orthosis device and the thread-guiding structure thereof are difficult to be assembled and cost-wasting to be used.

The present invention has arisen to mitigate and/or obviate the afore-described disadvantages.

SUMMARY OF THE INVENTION

The major object of the present invention is to provide an orthosis device and a thread-guiding structure thereof, which has a simple structure, and the present invention is cost-saving to be manufactured and time saving to be assembled.

To achieve the above and other objects, a thread-guiding structure is provided for being disposed on an orthosis device, including: a base, having a recess, the recess having an inner wall, the inner wall having a first restriction structure; and a guiding member, defining an axis, including a guiding groove and a second restriction structure which are integrally formed, the guiding groove being arcuately disposed about the axis, the guiding member received in the recess and positionably restricted with blocking of the second restriction structure and the first restriction structure, the guiding groove and the inner wall defining a thread-penetrating passage therebetween.

To achieve the above and other objects, an orthosis device is further provided, including the plurality of thread-guiding structures, further including: two board portions, spacingly arranged, each of the two board portions having at least one base; at least one rope body, each of the at least one rope body disposed through the thread-penetrating passage of at least one said base of each said board portion and arranged in two of the guiding grooves, wherein an axial movement of the at least one rope body operates to drive the two board portions close to or away from each other.

The present invention will become more obvious from the following description when taken in connection with the accompanying drawings, which show, for purpose of illustrations only, the preferred embodiment(s) in accordance with the present invention.

DETAILED DESCRIPTION OF THE PREFERRED EMBODIMENTS

Figure 1:
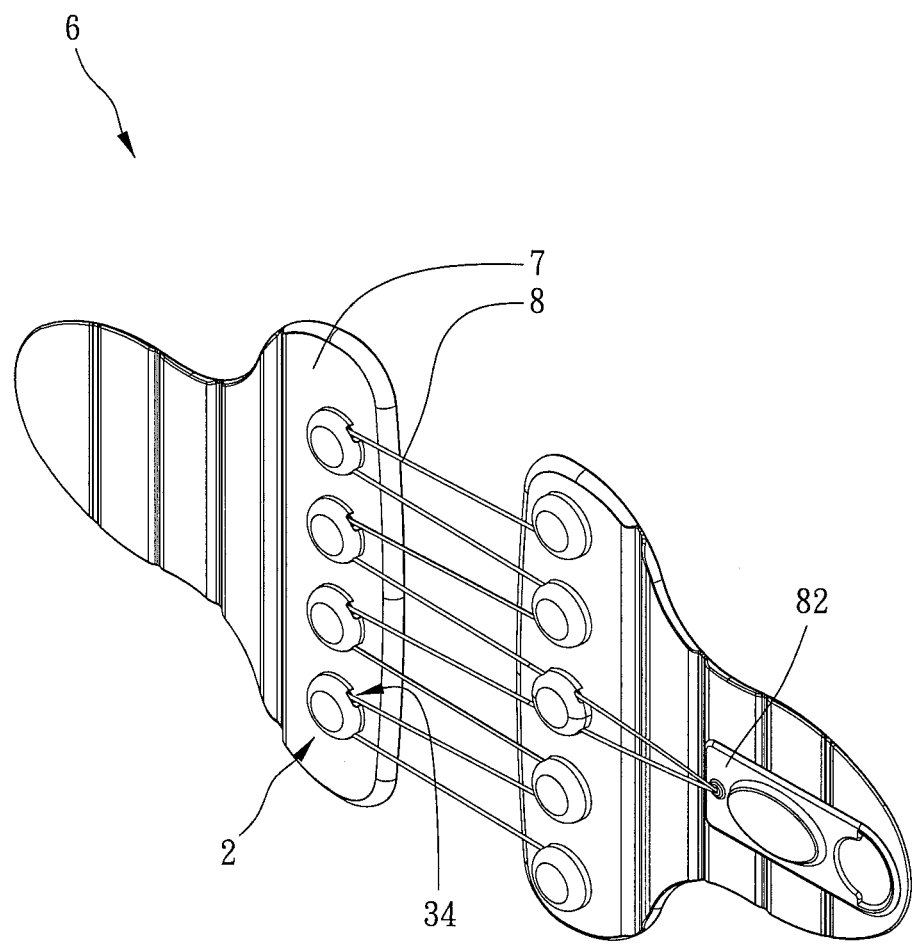
FIG. 1 is a perspective view of a preferred embodiment of the present invention.

The present invention will be clearer from the following description when viewed together with the accompanying drawings, which show, for purpose of illustrations only, the preferred embodiment in accordance with the present invention.

Please refer to FIGS. 1 to 8 for a preferred embodiment of the present invention. An orthosis device and a thread-guiding structure thereof include a thread-guiding structure 2 and an orthosis device 6.

The thread-guiding structure 2 includes a base 3 and a guiding member 4. The base 3 has a recess 31, the recess 31 has an inner wall 32, and the inner wall 32 has a first restriction structure 33. The guiding member 4 defines an axis 41 and includes a guiding groove 42 and a second restriction structure 43 which are integrally formed (please refer to FIGS. 6 and 7), the guiding groove 42 is arcuately disposed about the axis 41, and the guiding groove 42 has a smooth structure with a low friction so that when a wire passes therethrough, the wire can pass smoothly. The guiding member 4 is received in the recess 31 and positionably restricted with blocking of the second restriction structure 43 and the first restriction structure 33, the guiding groove 42 and the inner wall 32 define a thread-penetrating passage 44 therebetween for the wire to pass therethrough. Preferably, the guiding member 4 is rotatable relative to the recess 31 so that the wire can pass smoothly, and abrasions of the wire and the guiding member 4 can be effectively reduced. The base 3 further includes a plurality of connecting bridges 36 integrally formed thereon, wherein every adjacent two ones of the at least three recesses 31 are integrally connected with one of the plurality of connecting bridges 36.

Specifically, the first restriction structure 33 includes a first lower annular protrusion 331 disposed on a bottom portion of the recess 31 and a first upper annular protrusion 333 disposed on a peripheral side of the inner wall 32, the first lower annular protrusion 331 has a first lower flange 332 protruding radially, the second restriction structure 43 includes a second lower annular protrusion 431 disposed on a bottom portion of the guiding member 4 and a second upper annular protrusion 433 disposed on a peripheral side of the guiding member 4, the second lower annular protrusion 431 has a second lower flange 432 protruding radially, and the first and second lower flanges 332, 432 protrude toward opposite directions and are abuttable against each other axially, and the first and second upper annular protrusions 333, 433 abut against each other so that the guiding member 4 can be stably positioned in the recess 31. The first restriction structure 33 and the second restriction structure 43 allow the recess 31 and the guiding member 4 to be connected with each other stably. The guiding member 4 is integrally formed to simplify an assembling/disassembling process (if the guiding member 4 is not a structure integrally formed, there may be many elements thereof and the elements may get lost easily).

Figure 9:
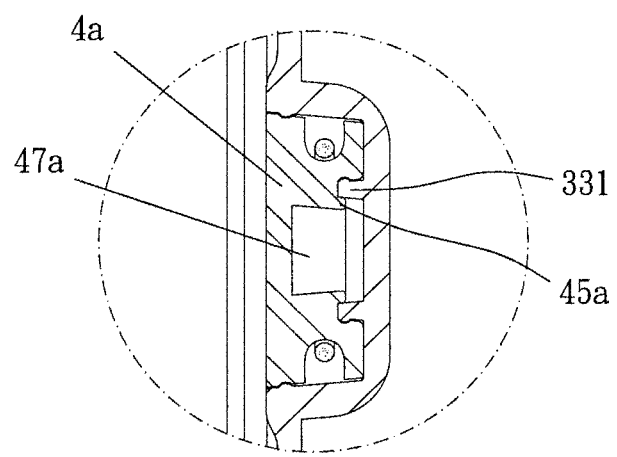

In this embodiment, the recess 31 is a basin-shaped shell, a peripheral side of the recess 31 has two through openings 34 communicating with the thread-penetrating passage 44, and the through opening 34 is for the wire to be disposed therethrough. The guiding member 4 is a round plate, the guiding groove 42 is annularly disposed on the round plate to make a lower portion of the guiding member 4 be a plate edge 48, and the plate edge 48 can restrict a movement of the guiding member 4 so that the guiding member 4 will not be dislocated from the recess 31. The base 3 further has a protrusive wall 35 disposed around a peripheral edge of the recess 31, and the guiding member 4 is preferably non-protrusive beyond the protrusive wall 35, the protrusive wall 35 can protect the guiding member 4 so that the movement of the guiding member 4 will not be influenced by collision or friction and a stability of the thread-guiding structure 2 is enhanced. A central portion of the guiding member 4 has a room 47, the room 47 opens toward the recess 31, and the room 47 allows the plate edge 48 to retract slightly and to be received in the recess 31. In another embodiment, a bottom portion of a guiding member 4a further includes an annular rib 45a protruding axially, and the annular rib 45a is inserted in the first lower annular protrusion 331 (as shown in FIG. 9) so that the annular rib 45a and the plate edge 48 can keep the guiding member 4a from being dislocated from the recess 31, and a room 47a allows the annular rib 45a to retract slightly and to be received in the first lower annular protrusion 331.

Figure 8:
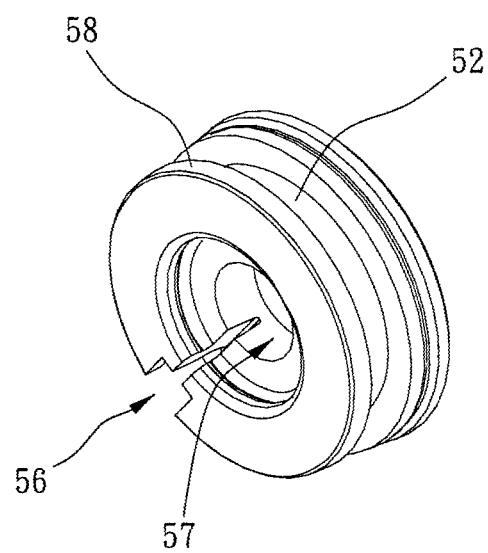
FIGS. 8 to 9 are drawings showing two embodiments of guiding members of the present invention.

The guiding member of the thread-guiding structure may be in other modes. As shown in FIG. 8, the guiding member 5 further includes at least one axial slit 56, the axial slit 56 goes radially through the plate edge 58, and the axial slit 56 communicates between the guiding groove 52 and the room 57. A distal end of the wire has a rope knot 81, the rope knot 81 is for being restricted in the axial slit 56 and located in the room 57 and fixes an end of a rope body 8. The axial slit 56 also allows the guiding member 5 to retract slightly and to be received in the recess 31. Preferably, the guiding member 5 may be arranged in the base 3 which the rope knot 81 is located in, and the guiding member 5 may also be arranged in other bases 3.

Figure 2:
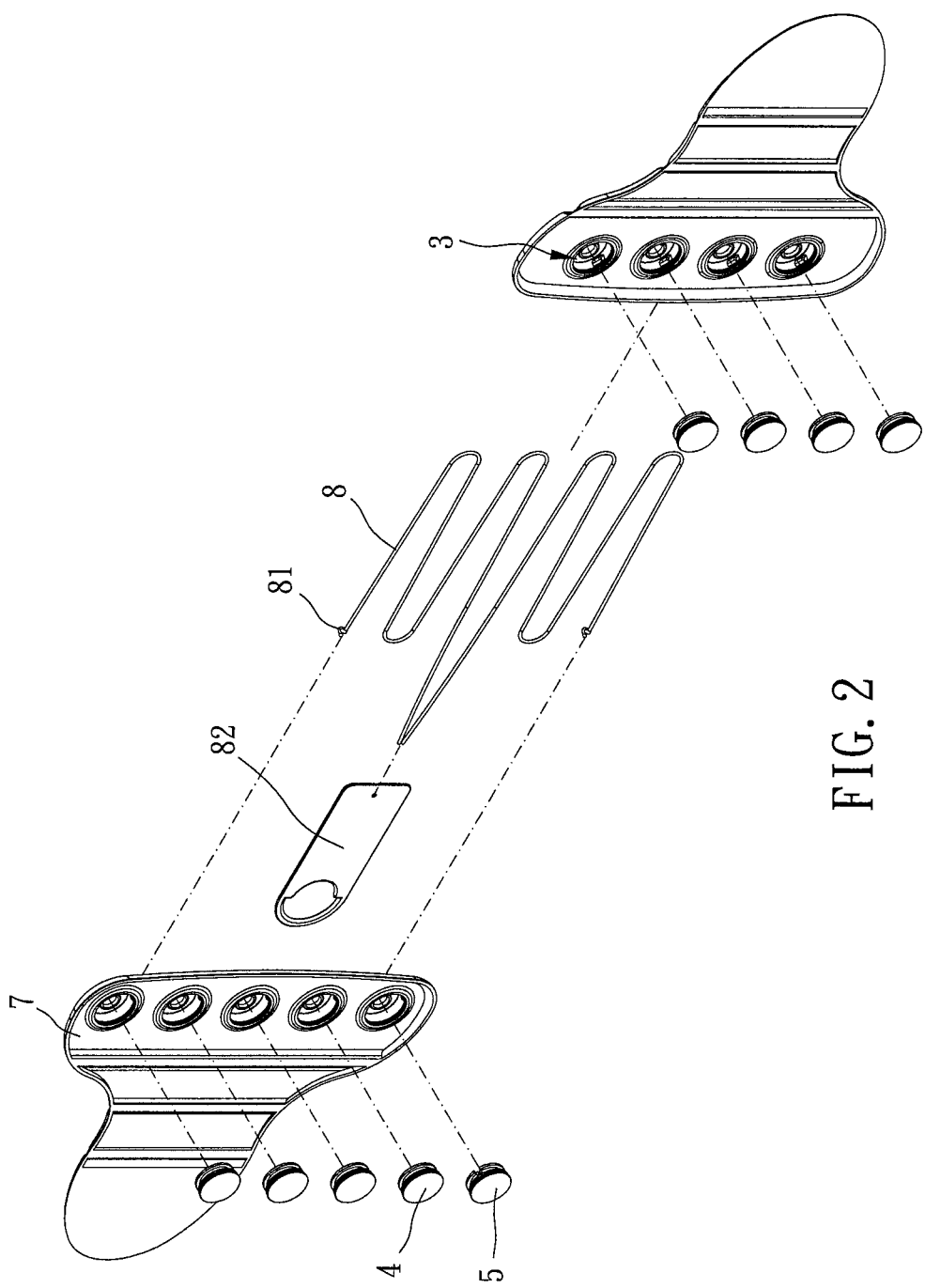
FIG. 2 is a breakdown view of the preferred embodiment of the present invention.
Figure 4:
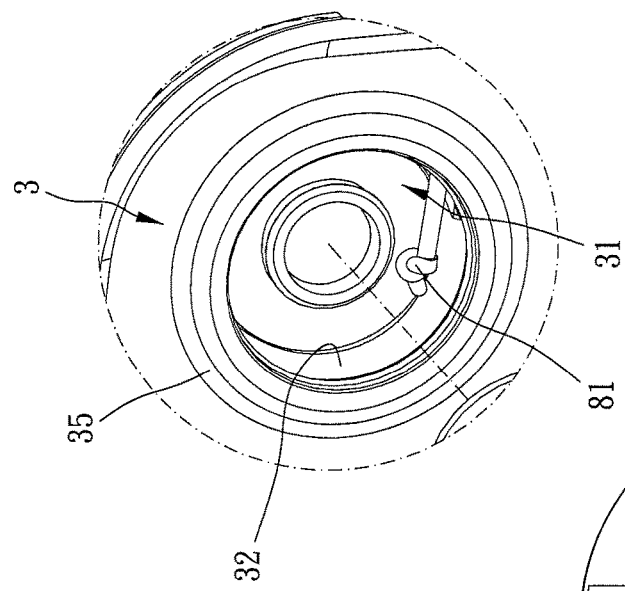
FIG. 4 is an enlarged view of FIG. 3.
Figure 3:
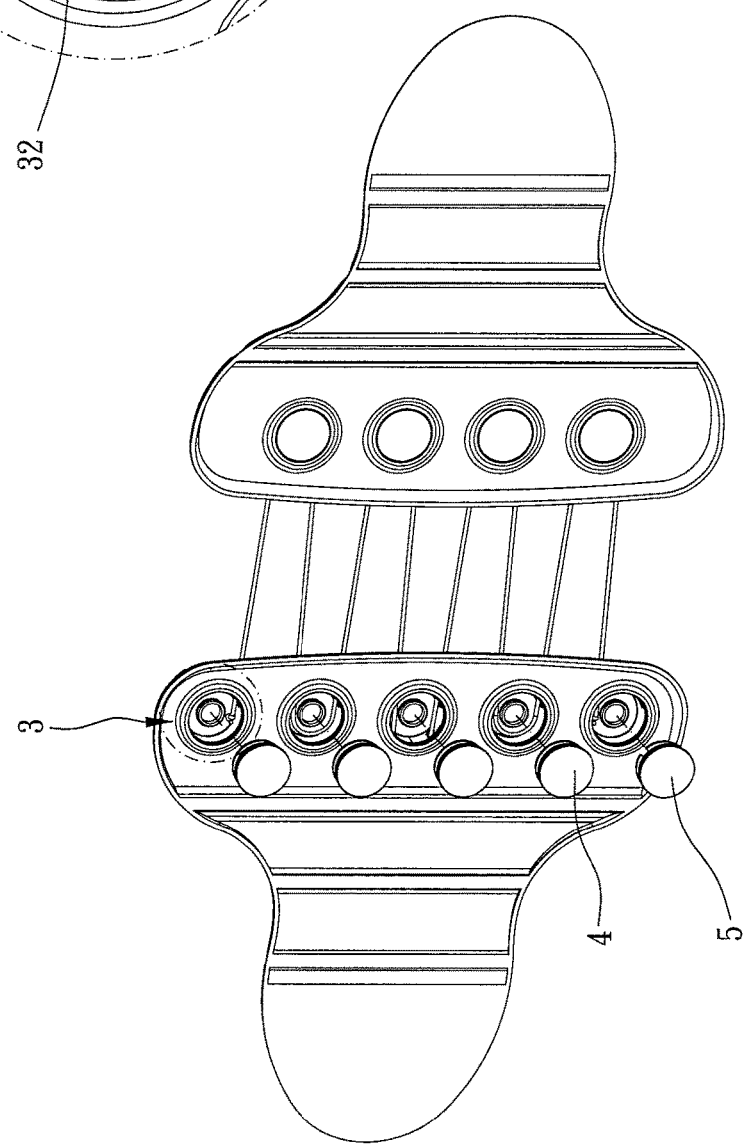
FIG. 3 is a partial breakdown view of the preferred embodiment of the present invention.
Figures 5, 6:
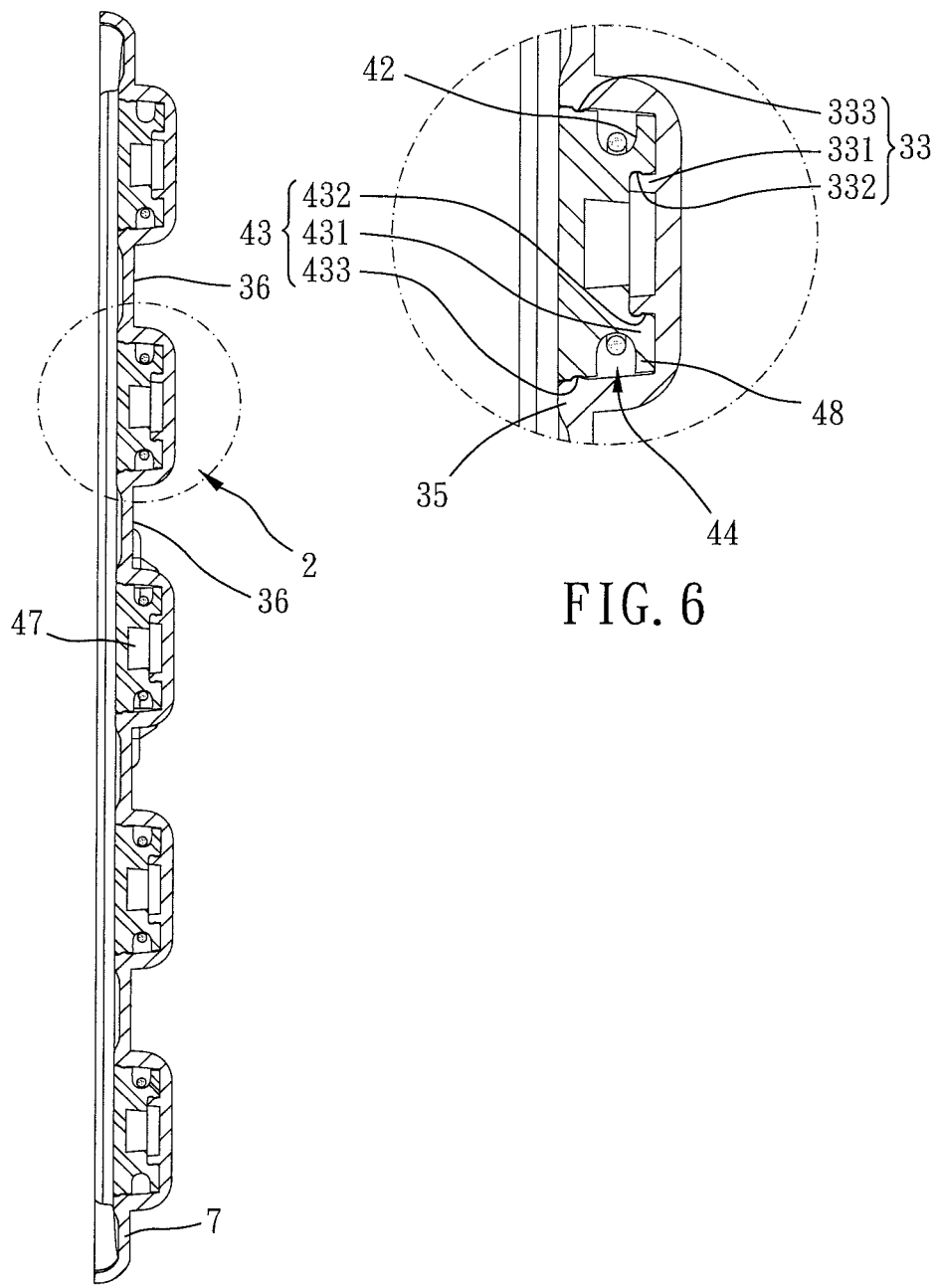
FIG. 5 is a cross-sectional view of the preferred embodiment of the present invention.
FIG. 6 is a partially-enlarged view of FIG. 5.
Figure 7:
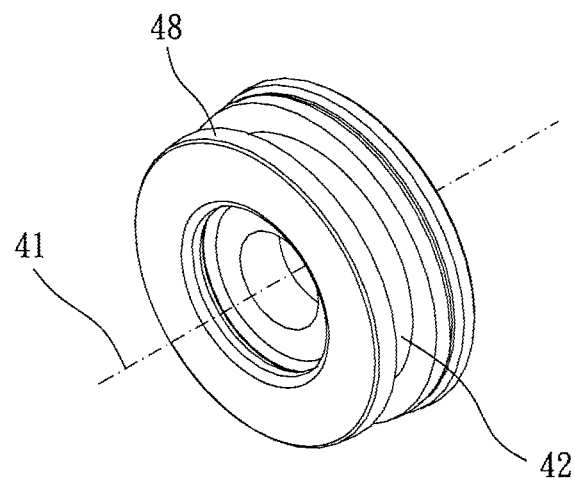
FIG. 7 is an enlarged view of a thread-guiding structure of another preferred embodiment of the present invention.

The orthosis device 6 includes the plurality of thread-guiding structures, two board portions 7 and at least one rope body 8. The two board portions 7 are spacingly arranged, and each of the two board portions 7 has at least one base 8. The plurality of thread-guiding structures include the plurality of guiding members 4 and at least one said guiding member 5, and the guiding member 5 is located in a distal end of the base 3 for restricting an end of the rope body 8. Each of the at least one rope body 8 is disposed through the thread-penetrating passage 44 of at least one said base 3 of each said board portion 7 and arranged in two of the guiding grooves 42 wherein an axial movement of the at least one rope body 8 operates to drive the two board portions 7 close to or away from each other. Preferably, a distal end of each of the at least one rope body 8 is fixed to a pull handle 82 to control the rope body 8 (as shown in FIGS. 1 and 2). The orthosis device 6 may be a protector or similar adjustable devices such as a wrist protector or an ankle protector.

In other embodiments, the first and second restriction structures of the thread-guiding structure may include only the first and second lower annular protrusions and without the first and second upper annular protrusions; or may include only the first and second upper annular protrusions and without the first and second lower annular protrusions. The guiding groove may be a structure having an unsmooth surface, and the guiding member may be rotatable relative to the recess. The rope knot of the rope body may be formed by knotting the rope body and melting the rope with high temperature or connected with a fixing sheet so as to fix the distal end of the rope body to the guiding member. The plurality of the guiding members may or may not include the axial slit. The guiding member may be in other shapes, such as semicircular, as long as the guiding member can assist the rope body to move and be positioned in the recess.

Given the above, the guiding member is integrally formed, so the guiding member can be easily disassembled and has a strong structure. Each of the at least one rope body is moved through the guiding groove having the smooth surface and the guiding member rotating.

While we have shown and described various embodiments in accordance with the present invention, it should be clear to those skilled in the art that further embodiments may be made without departing from the scope of the present invention.

What is claimed is:

1. A thread-guiding structure, for being disposed on an orthosis device, including:
    a base, having at least three recesses integrally formed thereon and a plurality of connecting bridges integrally formed thereon, each of the at least three recesses having an inner wall having a first restriction structure, every adjacent two ones of the at least three recesses being integrally connected with one of the plurality of connecting bridges;
    at least three guiding members, each of the at least three guiding members defining an axis, including a guiding groove arcuately disposed about the axis and a second restriction structure which are integrally formed, each of the at least three guiding members received in one of the at least three recesses and positionably restricted with blocking of the second restriction structure of one of the at least three guiding members and the first restriction structure of one of the at least three recesses, each guiding groove and one of the inner wall of the at least three recesses defining a thread-penetrating passage therebetween, each of the at least three guiding members being freely bidirectionally rotatable;
    wherein the first restriction structure includes a first lower annular protrusion integrally projecting axially from a bottom portion of the recess, the first lower annular protrusion has a first lower flange integrally protruding radially, the second restriction structure includes a second lower annular protrusion integrally projecting from a bottom portion of the guiding member, the second lower annular protrusion has a second lower flange integrally protruding radially, and the first and second lower flanges protrude toward opposite directions and are abuttable against each other axially.

2. The thread-guiding structure of claim 1, wherein the bottom portion of the guiding member further includes an annular rib integrally protruding axially, and the annular rib is inserted in the first lower annular protrusion.

3. The thread-guiding structure of claim 2, wherein the recess is a basin-shaped shell, a peripheral side of the recess has two through openings communicating with the thread-penetrating passage; the first restriction structure further includes a first upper annular protrusion integrally projecting from a peripheral side of the inner wall, the second restriction structure further includes a second upper annular protrusion integrally projecting from a peripheral side of the guiding member, and the first and second upper annular protrusions protrude toward opposite directions and are abuttable against each other axially; the guiding member is a round plate and rotatable relative to the recess, the guiding groove is annularly disposed on the round plate to make a lower portion of the guiding member be a plate edge; the base further has a protrusive wall integrally connected with and around a peripheral edge of the recess, and the guiding member is non-protrusive beyond the protrusive wall; the guiding member further includes at least one axial slit; a central portion of the guiding member has a room, the axial slit goes radially through the plate edge, the axial slit communicates between the guiding groove and the room, and the room opens toward the recess; the inner wall is linearly tapered from the second upper annular protrusion to the bottom portion of the recess.

4. The thread-guiding structure of claim 1, wherein the first restriction structure includes a first upper annular protrusion integrally projecting axially from a peripheral side of the inner wall, the second restriction structure includes a second upper annular protrusion integrally projecting from a peripheral side of the guiding member, and the first and second upper annular protrusions protrude toward opposite directions and are abuttable against each other axially.

5. The thread-guiding structure of claim 1, wherein the guiding member is a round plate, and the guiding groove is annularly disposed on the round plate.

6. The thread-guiding structure of claim 1, wherein the base further has a protrusive wall integrally connected with and around a peripheral edge of the recess, and the guiding member is non-protrusive beyond the protrusive wall.

7. The thread-guiding structure of claim 1, wherein the guiding member further includes at least one axial slit.

8. The thread-guiding structure of claim 1, wherein a central portion of the guiding member has a room, and the room opens toward the recess.

9. An orthosis device, including the thread-guiding structure of claim 1, further including:
two board portions, spacingly arranged, each of the two board portions having at least one of said base;
at least one rope body, each of the at least one rope body disposed through each thread-penetrating passage of the at least one of said base of each said board portion, wherein an axial movement of the at least one rope body operates to drive the two board portions close to or away from each other.

* * * * *